United States Patent [19]

Ogata et al.

[11] 4,248,869
[45] Feb. 3, 1981

[54] PHENYL ISOTHIOCYANATE DERIVATIVES AND THEIR PRODUCTION

[75] Inventors: Masaru Ogata, Kobe; Yoshihachi Watanabe, Shiga; Hiroshi Matsumoto, Takatsuki; Katsuya Tawara, Ibaraki, all of Japan

[73] Assignee: Shionogi & Co., Japan

[21] Appl. No.: 946,422

[22] Filed: Sep. 25, 1978

[30] Foreign Application Priority Data

Oct. 4, 1977 [JP] Japan .................... 52-119789

[51] Int. Cl.³ .................. A01N 41/00; C07D 307/64; C07C 161/04; C07D 265/00
[52] U.S. Cl. .................. 424/248.5; 260/454; 260/347.2; 544/160; 544/391; 424/250; 424/285; 424/302
[58] Field of Search .................. 260/454, 347.2; 544/160, 391; 424/248.5, 250, 285, 302

[56] References Cited

U.S. PATENT DOCUMENTS

| | | | |
|---|---|---|---|
| 3,231,596 | 1/1966 | Knusli et al. | 260/454 |
| 3,449,112 | 6/1969 | Lemin | 260/454 |
| 3,480,424 | 11/1969 | Lemin | 260/454 |

*Primary Examiner*—Henry R. Jiles
*Assistant Examiner*—Robert C. Whittenbaugh
*Attorney, Agent, or Firm*—Wenderoth, Lind & Ponack

[57] ABSTRACT

A compound of the formula:

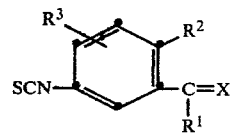

wherein
X is oxygen or sulfur;
$R^1$ is hydroxy, $C_1$-$C_4$ alkoxy, phenoxy, amino, $C_1$-$C_4$ alkylamino, $C_2$-$C_8$ dialkylamino, $C_6$-$C_{10}$ arylamino, tetrahydrofurfurylamino, morpholino or methylpiperazino, but when X is sulfur $R^1$ must be amino, $C_1$-$C_4$ alkylamino, $C_2$-$C_8$ dialkylamino or morpholino;
$R^2$ is $C_1$-$C_4$ alkoxy or $C_2$-$C_5$ alkoxycarbonyl;
$R^3$ is hydrogen, $C_1$-$C_4$ alkyl, $C_1$-$C_4$ alkoxy, $C_2$-$C_8$ dialkylamino or halogen and its salts being useful as agricultural fungicides are provided.

18 Claims, No Drawings

PHENYL ISOTHIOCYANATE DERIVATIVES AND THEIR PRODUCTION

The present invention relates to phenyl isothiocyanate derivatives. Some phenyl isothiocyanates have heretofore been known in Belgian Pat. No. 741,448; Canadian Patent 807,601; French Pat. No. 1,545,679; German Patent 2,013,788; British Pat. No. 1,183,113; Japanese Patent Publication No. 4,523/1973; Japanese Patent Unexamined Publications Nos. 18,626/1975; 1,023/1977; Dutch Pat. No. 67.12996; U.S. Pat. Nos. 3,530,161; 3,887,358, etc.

More particularly, this invention is directed to a compound of the formula:

(I)

$$\text{SCN} - \underset{R^3}{\overset{R^2}{\underset{|}{\bigcirc}}} - \underset{R^1}{\overset{C=X}{|}}$$

wherein

X is oxygen or sulfur;

$R^1$ is hydroxy $C_1$–$C_4$ alkoxy, phenoxy, amino, $C_1$–$C_4$ alkylamino, $C_2$–$C_8$ dialkylamino, $C_6$–$C_{10}$ arylamino, tetrahydrofurylamino, morpholino or methylpiperazino, but when X is sulfur $R^1$ must be amino, $C_1$–$C_4$ alkylamino, $C_2$–$C_8$ dialkylamino or morpholino;

$R^2$ is $C_1$–$C_4$ alkoxy or $C_2$–$C_5$ alkoxycarbonyl;

$R^3$ is hydrogen, $C_1$–$C_4$ alkyl, $C_1$–$C_4$ alkoxy, $C_2$–$C_8$ dialkylamino or halogen; and their salts being useful as agricultural fungicides.

Giving some additional explanations to the terms in the foregoing definition, "alkyl" refers to methyl, ethyl, propyl, isopropyl, butyl, isobutyl, t-butyl and the like; "alkoxy" refers to methoxy, ethoxy, propoxy, isopropoxy, butoxy, isobutoxy, t-butoxy and the like; "alkylamino" refers to methylamino, ethylamino, propylamino, isopropylamino, butylamino and the like; "dialkylamino" refers to dimethylamino, methylethylamino, diethylamino, ethylbutylamino, dibutylamino and the like; "arylamino" refers to phenylamino, tolylamino, xylylamino, mesitylamino, cumenylamino and the like; "alkoxycarbonyl" refers to methoxycarbonyl, ethoxycarbonyl, propoxycarbonyl, isopropoxycarbonyl, butoxycarbonyl and the like; "halogen" refers to fluoro, chloro, bromo, iodo and the like.

Up to this time, it has been known that such phenyl isothiocyanates are useful as germination regulators (Japanese Patent Unexamined Publication No. 1023/1977), and that p-ethoxycarbonylphenyl isothiocyanates are useful as agricultural fungicides (Canadian Pat. No. 807,601). However, the fungicidal activity of these compounds is insufficient for agricultural use.

The phenyl isothiocyanate derivatives (I) of the present invention are synthesized as shown in the following reaction scheme:

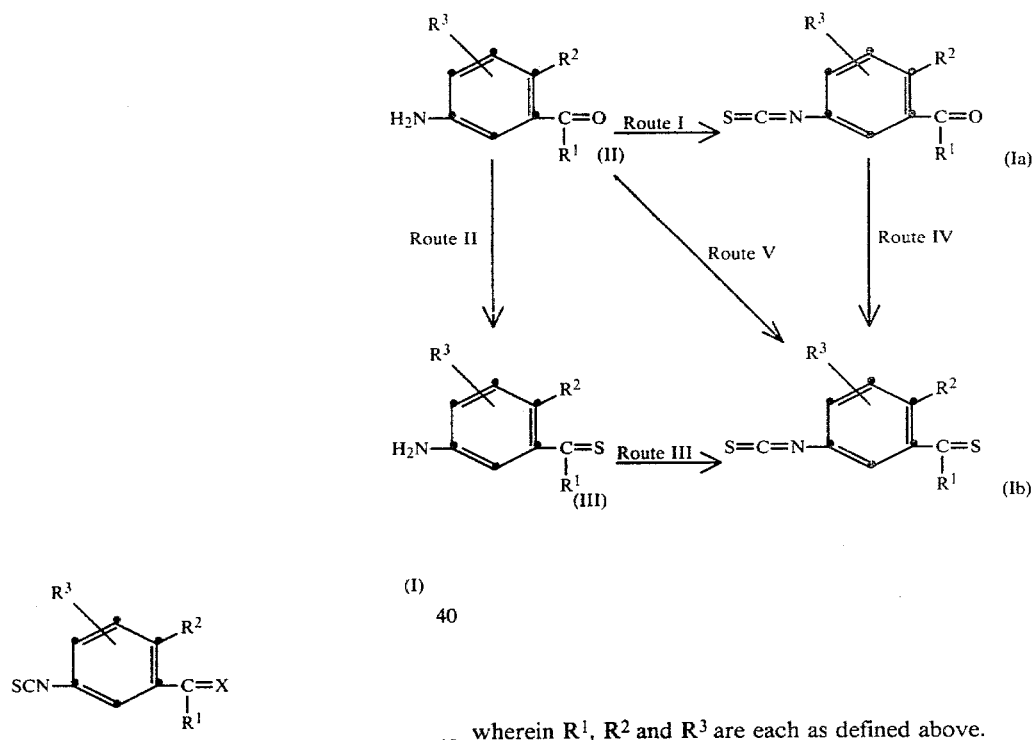

wherein $R^1$, $R^2$ and $R^3$ are each as defined above.

Route I

The isothiocyanate formation may be carried out in a conventional manner. The starting material (II) is reacted with carbon disulfide and a base (e.g. triethylamine, pyridine, dimethylamine) in an organic solvent, and the resulting intermediate is reacted with an alkyl halogenocarbonate (e.g. ethyl chlorocarbonate, methyl chlorocarbonate) with or without organic solvent. Thus phenyl isothiocyanates (Ia) are obtained.

Alternatively the phenyl isothiocyanates (Ia) are prepared by reacting the starting material (II) with a dialkylthiocarbamoyl halogenide (e.g. diethylthiocarbamoyl chloride) in an organic solvent.

The starting material (II) can be prepared by known methods. For example, 3-diethylcarbamoyl-4-methoxy-5-methylaniline is prepared from 2-methoxy-3-methyl-5-nitrobenzoyl chloride by two steps as follows:

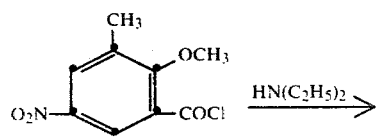

-continued

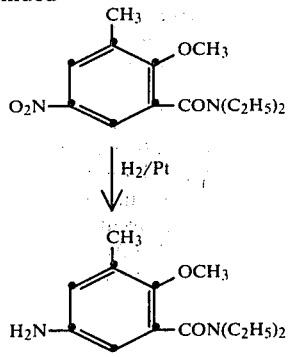

Route II
The convertion of carbamoyl group into thiocarbamoyl group is carried out by treating the starting material (II) with phosphorus pentasulfide in an organic solvent. Thus, thiocarbamoyl compound (III) is obtained.

Route III
The above obtained thiocarbamoyl compound (III) is subjected to the isothiocyanate formation. This route may be carried out in accordance with the procedure given in Route I. The thiocarbamoylaniline (III) can be obtained by reducing the corresponding nitrobenzene derivative:

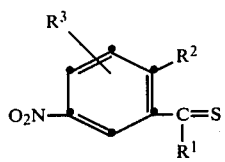

wherein $R^1$, $R^2$ and $R^3$ are each as defined above.
Thus, another product (Ib) is obtained.

Route IV
The first product (Ia) is subjected to the thiocarbamoyl group formation. This route may be carried out by treating with phosphorus pentasulfide or with a dialkylthiocarbamoyl halogenide/aluminum chloride each in an organic solvent. Thus, the second product (Ib) is obtained, too.

Route V
The second product (Ib) is directly prepared by treating the starting material (II) with a dialkylthiocarbamoyl halogenide/aluminum chloride in an organic solvent.

Any of these reactions are carried out at a temperature of about 0°–150° C., preferably 45°–100° C. Representatives of the organic solvent include tetrahydrofuran, benzene, toluene, ethylene dichloride, methylene chloride, chlorobenzene and the like.

Presently preferred and practical embodiments of the present invention are illustratively shown in the following examples.

EXAMPLE 1

To a solution of methyl 2-methoxy-4-methyl-5-aminobenzoate (975 mg) in tetrahydrofuran (5 ml) are added triethylamine (1.52 g) and carbon disulfide (1.14 g), and the resultant mixture is stirred at room temperature for 2.5 hours. Ethyl chlorocarbonate (1.63 g) is added to the mixture, which is stirred for additional 20 minutes at room temperature. A solution of sodium hydroxide (1.2 g) in water (32 ml) is added to the mixture, which is stirred for 15 minutes. The reaction mixture is mixed with an excess amount of water and shaken with methylene chloride. The organic layer is dried over Glauber's salt and the solvent is evaporated. The residue is dissolved in methylene chloride and chromatographed on a column of silica gel. Evaporating the solvent from the elution, the residue is dissolved in isopropyl ether and n-hexane is added thereto. The precipitated crystals are filtered to give 3-methoxycarbonyl-4-methoxy-6-methylphenyl isothiocyanate (952 mg) as crystals melting at 86°–87.5° C.

EXAMPLES 2–27

Using the following starting material (II), the reaction is carried out as in Example 1, whereby the corresponding product (Ia) is obtained:

| Ex. No. | II | | | | Ia mp(°C.) or |
|---|---|---|---|---|---|
| | $R^1$ | $R^2$ | $R^{3a}$ | $R^{3b}$ | $IR(cm^{-1})$ |
| 2 | OMe | OMe | H | H | 78.5–79.5 |
| 3 | OMe | OMe | H | OMe | 92–93 |
| 4 | OMe | OMe | Me | H | 2100, 1728 (CHCl$_3$) |
| 5 | OMe | OMe | OMe | H | 64–65 |
| 6 | OEt | OMe | H | Me | 60.5–61.5 |
| 7 | OMe | OEt | H | Me | 91–92 |
| 8 | O-i-Pr | OMe | H | Me | 2080, 1722 (film) |
| 9 | DMA | OMe | H | H | 2100, 1630 (CHCl$_3$) |
| 10 | DMA | OMe | H | Me | 161–162 |
| 11 | DMA | OMe | H | OMe | 184–185.5 |
| 12 | DMA | OMe | Me | H | 74.0–75.0 |
| 13 | DMA | OMe | OMe | H | 2100, 1629 (CHCl$_3$) |
| 14 | OPh | OMe | H | Me | 174.5–175.5 |
| 15 | N-morpholino | OMe | H | Me | 162.5–163.5 |
| 16 | N-methylpiperazino | OMe | H | Me | 155.5–156.5 |
| 17 | NHMe | OMe | H | Me | 191.5–192.5 |
| 18 | NHMe | OMe | H | OMe | 187–188 |
| 19 | NHMe | OMe | Me | H | 128–129 |
| 20 | NHMe | OMe | OMe | H | 129–130 |
| 21 | NH$_2$ | OMe | H | Me | 206–207 |
| 22 | NH$_2$ | OMe | H | OMe | 224–226 |
| 23 | NH$_2$ | OMe | OMe | H | 161–162 |
| 24 | OMe | COOEt | H | H | 1728, 1760, 2090 (film) |
| 25 | DEA | OMe | H | H | 90–91 |
| 26 | DEAEA | OMe | H | Me | 93–94 |
| 27 | OMe | OMe | H | DMA | 103–103.5 |

Note:
The abbreviations in the Table have the following meanings: H (hydrogen), Me (mrthyl group), Et (ethyl group), Pr (propyl group), Ph (phenyl group), DMA (dimethylamino group), DEA (diethylamino group), DEAEA (diethylaminoethylamino group), i- (iso-), mp (melting point), IR (infrared spectrum).

EXAMPLE 28

A mixture of 3-[N-(2,6-dimethylphenyl)carbamoyl]-4-methoxy-6-chloroaniline (650 mg), diethylthiocarbamoyl chloride (360 mg) and chlorobenzene (6 ml) is refluxed for 30 minutes. The reaction mixture is mixed with water and shaken with methylene chloride. The organic layer is washed with water, dried over Glauber's salt and concentrated to remove the solvent. The residue is chromatographed on a column of silica gel, which is eluted with methylene chloride. The eluted fractions are collected and the solvent is evaporated. The residue is recrystallized from ethyl acetate to give 3-[N-(2,6-dimethylphenyl)carbamoyl]-4-methoxy-6-chlorophenyl isothiocyanate (340 mg) as crystals melting at 191°–192.5° C.

EXAMPLE 29-33

Using the following starting material (II), the reaction is carried out as in Example 28, whereby the following product (Ia) is obtained:

$R^{3b}$—[benzene ring with $R^2$, $H_2N$, $COR^1$] (II) → $R^{3b}$—[benzene ring with $R^2$, SCN, $COR^1$] (Ia)

| Ex. No. | II | | | Ia |
|---|---|---|---|---|
| | $R^1$ | $R^2$ | $R^{3b}$ | mp(°C.) |
| 29 | OMe | OMe | Cl | 98–99 |
| 30 | DMA | OMe | Cl | 195–196.5 |
| 31 | NHMe· | OMe | Cl | 192–195 |
| 32 | NH—[ring]—O | | OMe | Cl | 167–168 |
| 33 | OH | OMe | Me | 181–183 |

Note:
The abbreviations in the Table have the same meanings as defined above.

EXAMPLE 34

(a) To a solution of 3-dimethylcarbamoyl-4-methoxy-5-methylnitrobenzene (1.10 g) in benzene (11 ml) is added phosphorus pentasulfide (3.08 g), and the resultant mixture is refluxed for 1 hour. After sooling, the reaction mixture is mixed with icy water and shaken with ether. The organic layer is washed with water, dried over Glauber's salt and concentrated under reduced pressure to remove the solvent. The residue is chromatographed on a column of silica gel, which is eluted with benzene, methylene chloride and then methylene chloride/2% methanol in order. The eluted fractions are concentrated under reduced pressure and the residue is washed with isopropyl ether to give 3-dimethylthiocarbamoyl-4-methoxy-5-methyl-nitrobenzene (1.0 g) as crystals melting at 138°–139° C.

(b) To a solution of above product (0.95 g) in methanol (30 ml) is added platinum dioxide hydrate (0.20 g), and the resultant mixture is shaken in hydrogen stream, until the absorption of hydrogen stops. The reaction mixture is filtered to remove the catalyst and the filtrate is concentrated under reduced pressure. The residue is dissolved in methylene chloride, dried over Glauber's salt and the solvent is evaporated. The residue is dissolved in dry tetrahydrofuran (5 ml) to give a solution, which is mixed with triethylamine (1.13 g) and carbon disulfide (0.85 g). The resultant mixture is stirred at ordinary temperature overnight. Ethyl chlorocarbonate (1.22 g) is added to the mixture under cooling, which is stirred for 45 minutes under cooling. The mixture is treated with 10% aqueous sodium hydroxide (9 ml) and shaken with methylene chloride. The organic layer is washed with water, dried over Glauber's salt and the solvent is evaporated. The residue is chromatographed on a column of silica gel, which is eluted with methylene chloride. After evaporating the solvent, the fraction affords a brown oil (0.87 g), which is recrystallized from isopropyl etherpetroleum ether to give 3-dimethylthiocarbamoyl-4-methoxy-5-methylphenyl isothiocyanate (312 mg) as crystals melting at 74°–75° C.

EXAMPLE 35

To a solution of 3-dimethylcarbamoyl-4-methoxy-5-methylaniline (600 mg) in dry ethylene dichloride (12 ml) is added diethylthiocarbamoyl chloride (850 mg), and the resultant mixture is refluxed for 25 minutes. Aluminum chloride (360 mg) is added to the mixture, which is refluxed for 2 hours. After cooling, the mixture is mixed with aqueous sodium bicarbonate, stirred at room temperature for 15 minutes and shaken with methylene chloride. The organic layer is washed with water, dried over Glauber's salt and the solvent is evaporated under reduced pressure. The residue is chromatographed on a column of silica gel, which is eluted with methylene chloride. The eluted fraction is evaporated, and the residue is washed with isopropyl ether-petroleum ether to give 3-dimethylthiocarbamoyl-4-methoxy-5-methylphenyl isothiocyanate (214 mg) as crystals melting at 74°–75° C.

EXAMPLE 36

Using 3-diethylcarbamoyl-4-methoxyphenyl isothiocyanate (700 mg), the reaction is carried out as in Example 35, whereby 3-diethylthiocarbamoyl-4-methoxyphenyl isothiocyanate (437 mg) is obtained as colorless needles melting at 121°–122° C.

EXAMPLES 37-39

The following compounds are obtained by carrying out the reaction as in Example 34 (a).

| Ex. No. | | |
|---|---|---|
| 37 | $CH_3$—[benzene]—$OCH_3$, SCN, C(=S)—N[morpholine ring]O | m.p. 202.5–204° C. |
| 38 | $CH_3O$—[benzene]—$OCH_3$, SCN, C(=S)—NH—$CH_3$ | m.p. 165–166° C. |
| 39 | $CH_3O$—[benzene]—$OCH_3$, SCN, C(=S)—$NH_2$ | m.p. > 250° C. |

The phenyl isothiocyanates (I) are useful as agricultural fungicides against various phytopathogenic fungi such as cucurbitaceae powdery mildew, cucurbitaceae downy mildew, cucurbitaceae anthracnose, rice plant blast and drooping diseases of various crops. Excellent control effect of the product (I) is illustratively shown by the following experiments. The list indicates test compounds used in the experiments.

| Compd. No. | Structural Formula | Chemical Name | Note |
|---|---|---|---|
| 1. | (benzene ring with SCN, OCH₃, COOCH₃) | 3-Methoxycarbonyl-4-methoxyphenyl isothiocyanate | |
| 2. | (benzene ring with CH₃, SCN, OCH₃, COOCH₃) | 3-Methoxycarbonyl-4-methoxy-6-methyl-phenyl isothiocyanate | |
| 3. | (benzene ring with CH₃O, SCN, OCH₃, COOCH₃) | 3-Methoxycarbonyl-4,6-dimethoxyphenyl isothiocyanate | |
| 4. | (benzene ring with OCH₃, SCN, OCH₃, COOCH₃) | 3-Methoxycarbonyl-4,5-dimethoxyphenyl isothiocyanate | |
| 5. | (benzene ring with SCN, OCH₃, CON(CH₃)₂) | 3-Dimethylcarbamoyl-4-methoxyphenyl isothiocyanate | |
| 6. | (benzene ring with CH₃, SCN, OCH₃, COOCH(CH₃)₂) | 3-Isopropoxycarbonyl-4-methoxy-6-methyl-phenyl isothiocyanate | |
| 7. | (benzene ring with CH₃, SCN, OCH₃, COOCH₃) | 3-Methoxycarbonyl-4-methoxy-5-methyl-phenyl isothiocyanate | |
| 8. | (benzene ring with CH₃, SCN, OC₂H₅, COOCH₃) | 3-Methoxycarbonyl-4-ethoxy-6-methyl-phenyl isothiocyanate | |
| 9. | (benzene ring with CH₃, SCN, OCH₃, COOC₂H₅) | 3-Ethoxycarbonyl-4-methoxy-6-methyl-phenyl isothiocyanate | |
| 10. | CH₂NHC(=S)−S\\Mn/S−C(=S)NHCH₂ | Manganese ethylene bisdithiocarbamic acid (mannev) | control |
| 11. | (CH₃)₂NSO₂NS−C(Cl)(F)(Cl) with phenyl | N'-Dichlorofluoro-methylthio-N,N-dimethyl-N'-phenyl-sulfamide (dichlofluanide) | control |
| 12. | (quinoxaline dithiolo structure with CH₃, C=O) | 6-Methyl-1,3-dithiolo-[4,5-b]-quinoxalin-2-on (quinomethionate) | control |
| 13. | C₂H₅O−P(=O)(S−Ph)(S−Ph) | p-Ethyl-s,s-diphenyl-phosphorodithiolate (EDDP) | control |
| 14. | (isoxazole with OH, CH₃) | 3-Hydroxy-5-methyl-isoxazole (hydroxyisoxazole) | control |

EXPERIMENT 1

Test for control effect against cucumber anthracnose

Seeds of cucumber (cultivar: Matsukaze) were sown in a vinyl chloride-cup of 9 cm in diameter containing soil, one seed per cup, in a greenhouse. When the primary leaf was developed, 5 ml of a solution of the test compound at a prescribed concentration was applied per cup. After application, the cups were kept at a temperature of 25°–26° C. and humidity of 80% for 1 day. A spore suspension of cucumber anthracnose (*Colletotrichum lagenarium*) was inoculated onto the aforementioned primary leaves of cucumber, five spots per leaf. The cups were kept at a temperature of 25° C. and humidity of 95% for 1 day. After allowing to stand at a temperature of 25° C. and humidity of 75-80% for 6 days, diseased degree in the inoculated portions was observed. Percent disease control was calculated using the following formula:

Percent Disease Control (%) = 
$$\frac{\text{Diseased Degree in Untreated Plot} - \text{Diseased Degree in Treated Plot}}{\text{Diseased Degree in Untreated Plot}} \times 100$$

Results are indicated in Table 1.

TABLE 1

| Test Compound No. | Concentration (ppm) | Diseased Degree | Percent Disease Control (%) |
|---|---|---|---|
| 1 | 500 | 0 | 100.0 |
| 2 | 500 | 0 | 100.0 |
| 3 | 500 | 0 | 100.0 |
| 4 | 500 | 0 | 100.0 |
| 8 | 500 | 0 | 100.0 |
| 9 | 500 | 0 | 100.0 |
| 10 | 1440 | 0 | 100.0 |
| Untreated Plot | — | 25 | 0.0 |

EXPERIMENT 2

Test for control effect against cucumber downy mildew

Seeds of cucumber (cultivar: Matsukaze) were sown in a vinyl chloride-cup of 9 cm in diameter containing soil, one seed per cup, in a greenhouse. When the primary leaf was developed, 5 ml of the solution of the test compounds at a prescribed concentration was applied per cup. After application, the cups were kept at a temperature of 20°-22° C. for 1 day. A spore suspension of cucumber downy mildew (*Pseudoperonospora cubensis*) was inoculated onto the aforementioned primary leaves of cucumber, five spots per leaf. The cups were kept at a temperature of 20° C. and humidity of 95% for 10 days. Diseased degree in the inoculated portions was observed. Percent disease control was calculated using the following formula:

Percent Disease Control (%) =
$$\frac{\text{Diseased Degree in Untreated Plot} - \text{Diseased Degree in Treated Plot}}{\text{Diseased Degree in Untreated Plot}} \times 100$$

Results are indicated in Table 2.

TABLE 2

| Test Compound No. | Concentration (ppm) | Diseased Degree | Percent Disease Control (%) |
|---|---|---|---|
| 1 | 500 | 0 | 100 |
| 2 | 500 | 0 | 100 |
| 3 | 500 | 0 | 100 |
| 4 | 500 | 0 | 100 |
| 6 | 500 | 0 | 100 |
| 8 | 500 | 0 | 100 |
| 11 | 500 | 0 | 100 |
| Untreated Plot | — | 100 | 0 |

EXPERIMENT 3

Test for control effect against cucumber powdery mildew

Seeds of cucumber (cultivar: Matsukaze) were sown in a vinyl chloride-cup of 9 cm in diameter containing soil, one seed per cup, in a greenhouse. When the primary leaf was developed, 5 ml of the solution of the test compounds at a prescribed concentration was applied per cup. After application, the cups were kept at a temperature of 25°-26° C. for 1 day. Leaves of cucumber infected by pathogenic fungi of the powdery mildew (*Sphaerotheca fuliginea*) were taken, and lesions covered with oidia were cut out in 1 square centimeter pieces. The fungi were inoculated to the primary leaves in the cups by sticking the oidia covered pieces onto them, four plots per leaf. The cups were then kept at a temperature of 25°-26° C. for 10 days. The oidium formation on the inoculated leaves was observed by microscope.

+: Infected spots and formation of numbers of oidia observed on the inoculated portions.

—: Neither infected spot nor oidium formation observed

Results are indicated in Table 3.

TABLE 3

| Test Compound No. | Concentration (ppm) | Diseased Degree |
|---|---|---|
| 1 | 500 | — |
| 2 | 500 | — |
| 3 | 500 | — |
| 4 | 500 | — |
| 7 | 500 | — |
| 8 | 500 | — |
| 12 | 125 | — |
| Untreaed Plot | — | + |

EXPERIMENT 4

Test for control effect against rice plant blast

Seedlings of rice plant (cultivar: Aichi-asahi), reared for 10 days in the greenhouse, were transplanted in a vinyl chloride-cup of 12 cm in diameter containing soil. A solution of the test compound at a prescribed concentration was applied 14 days after the transplantation. One day after the application, a spore suspension of pathogenic fungi of rice plant blast (*Pyricularia oryzae*) was sprayed on the leaf blade of the seedilings. The cups were kept in an infection room at a temperature of 28° C. and humidity of 98% for 24 hours. Then, they were kept at a temperature of 28° C. and humidity of 90% for 7 days in a greenhouse. Number of spots on the inoculated leaves was observed, and percent disease control was calculated using the following formula:

Percent Disease Control (%) =
$$\frac{\text{Number of Spots in Untreated Plot} - \text{Number of Spots in Treated Plot}}{\text{Number of Spots in Untreated Plot}} \times 100$$

Results are indicated in Table 4.

TABLE 4

| Test Compound No. | Concentration (ppm) | Number of Spots | Percent Disease Control (%) |
|---|---|---|---|
| 1 | 500 | 4 | 99.8 |
| 2 | 500 | 92 | 96.3 |
| 3 | 500 | 11 | 99.6 |
| 4 | 500 | 4 | 99.8 |
| 5 | 500 | 23 | 99.1 |
| 6 | 500 | 143 | 94.3 |
| 8 | 500 | 331 | 86.8 |
| 9 | 500 | 567 | 77.4 |
| 13 | 300 | 17 | 99.3 |
| Untreated Plot | — | 2515 | 0 |

EXPERIMENT 5

Test for control effect against damping-off of cucumber seedlings

One hundred and fifty ml of sterile soil was placed into a pot of 9 cm in diameter, and 20 cucumber seeds were sowed per pot. After cultivating fungi of the cucumber damping-off (*Pythium aphanidermatum, Fusarium oxysoirum, Rhizoctonia solani*) in a wheat bran medium for 5 days, it was mixed with sterile soil and cultured again for 2 days at a temperature of 25° C. Thirty ml of the solution of the test compounds at a prescribed concentration was drenched to each pot. The pots were kept at a temperature of 28° C. for 11 days in a greenhouse. Diseased degree in the treated pots was observed. Diseased degree and percent disease control were calculated using the following formulae:

Index of damping-off
1. Not germinated
2. Wilt and rot
3. Invasion more than ⅓ seedlings
4. Invasion not more than ⅓ seedlings
5. Seedlings sound Diseased Degree (%) =
$$\frac{(1 \times 4 + 2 \times 3 + 3 \times 2 + 4 \times 1 + 5 \times 0)}{\text{Number of observed cucumber} \times 4} \times 100$$

Percent Diseased Control (%) =
$$\frac{\text{Diseased Degree in Untreated Plot} - \text{Diseased Degree in Treated Plot}}{\text{Diseased Degree in Untreated Plot}} \times 100$$

Results are indicated in Table 5.

TABLE 5

| Test Compound No. | Concentration (ppm) | Rhizoctonia solani Diseased Degree | Rhizoctonia solani Percent Disease Control (%) | Pythium aphanidermatum Diseased Degree | Pythium aphanidermatum Percent Disease Control (%) | Fusarium oxysporum Diseased Degree | Fusarium oxysporum Percent Disease Control (%) |
|---|---|---|---|---|---|---|---|
| 1 | 500 | 28.8 | 71.2 | 36.3 | 63.7 | 65.0 | 7.9 |
| 4 | 500 | 0 | 100 | 76.3 | 23.7 | 10.0 | 85.8 |
| 5 | 500 | 36.3 | 63.7 | 0 | 100 | 22.5 | 68.1 |
| 6 | 500 | 28.8 | 71.2 | 85.0 | 15.0 | 10.0 | 85.8 |
| 7 | 500 | 56.3 | 43.7 | 100 | 0 | 27.5 | 61.0 |
| 8 | 500 | 66.0 | 34.0 | 100 | 0 | 18.8 | 73.4 |
| 14 | 500 | 62.5 | 37.5 | 21.3 | 78.7 | 25.0 | 64.6 |
| Untreated Plot | — | 100 | 0 | 100 | 0 | 100 | 0 |

Accordingly, the phenyl isothiocyanates (I) showed patent fungicidal activity against cucumber anthracnose, cucmber downy mildew, cucumber powdery mildew, rice plant blast, and damping-off of cucumber seedlings. The other compounds (I) also showed similar fungicidal activity.

The product (I) of this invention may be applied in a form suitable for agricultural fungicides, such as emulsions, solutions, wettable powders, dusts, suspensions, granules, aerosols, oils, smokes, pastes and the like. The compound (I) may be applied singly or in combination with solid or liquid carriers. Representatives of the solid carriers include clay, talc, diatomaceous earth, silica, kaolin, bentonite, pumice and the like. Examples of the liquid carriers are water, methanol, ethanol, ethylene glycol, dimethylformamide, dimethylsulfoxide, acetone, methyl ethyl ketone, cellosolve, dioxane, diglyme, and the like. If necessary, there may be added appropriate adjuvants such as emulsifiers, dispersants, spreaders, surfactants, wetting agents, stabilizers, synergists and the like. Moreover, the compound (I) may be used in combination with other agricultural chemicals such as other fungicides, germicides, insecticides, herbicides, repellents, miticides, nematocides, plant growth regulators and the like. Application rate of the compound (I) for liquid formulations is in the range of about 50–2,000 ppm, preferably 100–1,000 ppm and about 100–200 L per 10 are; and application rate for solid formulations is about 3–4 kg per 10 are.

Fungicidal compositions containing the compound (I) are illustratively shown in the following Formulations.

Formulation 1

Fifty parts by weight of 3-methoxycarbonyl-4-methoxyphenyl isothiocyanate, 35 parts by weight of diatomaceous earth, 10 parts by weight of white carbon, 2 parts by weight of sodium alkylbenzenesulfonate and 3 parts by weight of calcium lignin sulfonate are triturated and mixed to provide wettable powder.

Formulation 2

Thirty parts by weight of 3-methoxycarbonyl-4,6-dimethoxyphenyl isothiocyanate, 40 parts by weight of xylene, 20 parts by weight of cyclohexanone, and 10 parts by weight of polyoxyethylene alkyl aryl ether are mixed and stirred to provide an emulsion.

Formulation 3

Three parts by weight of 3-methoxycarbonyl-4,5-dimethoxyphenyl isothiocyanate, 7 parts by weight of talc and 90 parts by weight of clay are mixed and triturated to provide a dust formulation.

Formulation 4

Three parts by weight of 3-methoxycarbonyl-4,6-dimethoxyphenyl isothiocyanate, 2 parts by weight of sodium alkylbenzenesulfonate, 45 parts by weight of clay and 50 parts by weight of bentonite are mixed, kneaded with a suitable amount of water and granulated by an extrusive granulator. Air-drying at 50° C. and sieving through a 20–40 mesh screen provides the desired granules. Such granules are directly applied.

Further, the phenyl isothiocyanates (I) are also hopeful as antifungal agents in humans and animals. For example, 3-methoxycarbonyl-4,5-dimethoxyphenyl isothiocyanate showed a minimum inhibitory concentration of 6.2 γ/ml against *Candida albicans* M-9 in in vitro test.

What is claimed is:

1. A compound of the formula:

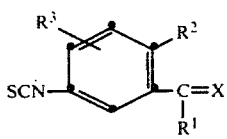

wherein

X is oxygen or sulfur;

R¹ is phenoxy, amino, methylamino, ethylamino, propylamino, isopropylamino, butylamino, dimethylamino, methylethylamino, diethylamino, ethylbutylamino, dibutylamino, phenylamino, tolylamino, xylylamino, mesitylamino, cumenylamino, tetrahydrofurfurylamino, morpholino or methylpiperazino, but when X is sulfur R¹ is amino, methylamino, ethylamino, propylamino, isopropylamino, butylamino, dimethylamino, methylethylamino, diethylamino, ethylbutylamino, dibutylamino, or morpholino;

R² is methoxy, ethoxy, propoxy, isopropoxy, butoxy, isobutoxy or t-butoxy;

R³ is hydrogen, methyl, ethyl, propyl, isopropyl, butyl, isobutyl, t-butyl, methoxy, ethoxy, propoxy, isopropoxy, butoxy, isobutoxy, t-butoxy, dimethylamino, methylethylamino, diethylamino, ethylbutylamino, dibutylamino, fluoro, chloro, bromo or iodo;

and salts thereof.

2. A compound according to claim 1, namely 3-dimethylcarbamoyl-4-methoxyphenyl isothiocyanate.

3. A compound according to claim 1, namely 5-dimethylcarbamoyl-4-methoxy-2-tolyl isothiocyanate.

4. A compound according to claim 1, namely 2,4-dimethoxy-5-dimethylcarbamoylphenyl isothiocyanate.

5. A compound according to claim 1, namely 5-dimethylcarbamoyl-4-methoxy-3-tolyl isothiocyanate.

6. A compound according to claim 1, namely, 3,4-dimethoxy-5-dimethylcarbamoylphenyl isothiocyanate.

7. A compound according to claim 1, namely 4-methoxy-5-phenoxycarboxyl-2-tolyl isothiocyanate.

8. A compound according to claim 1, namely 4-methoxy-5-morpholinocarbonyl-2-tolyl isothiocyanate.

9. A compound according to claim 1, namely 4-methoxy-5-(4-methylpiperazinocarbonyl)-2-tolyl isothiocyanate.

10. A compound according to claim 1, namely 4-methoxy-5-methylcarbamoyl-2-tolyl isothiocyanate.

11. A compound according to claim 1, namely 2,4-dimethoxy-5-methylcarbamoylphenyl isothiocyanate.

12. A compound selected from the group consisting of (a) 4-methoxy-5-methylcarbamoyl-2-tolyl isothiocyanate;

(b) 3,4-dimethoxy-5-methylcarbamoylphenyl isothiocyanate;

(c) 5-carbamoyl-4-methoxy-2-tolyl isothiocyanate;

(d) 5-carbamoyl-2,4-dimethoxyphenyl isothiocyanate;

(e) 5-carbamoyl-3,4-dimethoxyphenyl isothiocyanate;

(f) 3-dimethylcarbamoyl-4-methoxyphenyl isothiocyanate;

(g) 3-[N-(2,6-dimethylphenyl)carbamoyl]-4-methoxy-6-chlorophenyl isothiocyanate;

(h) 2-chloro-5-dimethylcarbamoyl-4-methoxyphenyl isothiocyanate;

(i) 2-chloro-5-methylcarbamoyl-4-methoxyphenyl isothiocyanate; and (j) 2-chloro-4-methoxy-5-(2,3,4,5-tetrahydrofurfuryl)carbamoylphenyl isothiocyanate.

13. A compound selected from the group consisting of (a) 3-dimethylthiocarbamoyl-4-methoxy-5-methylphenyl isothiocyanate and (b) 3-diethylthiocarbamoyl-4-methoxyphenyl isothiocyanate.

14. A compound according to claim 1, namely 3-dimethylcarbamoyl-4-methoxy-5-methylphenyl isothiocyanate.

15. A compound according to claim 1, wherein X is sulfur; R¹ is amino, methylamino, dimethylamino or morpholino; R² is methoxy; and R³ is hydrogen, chlorine, methyl or methoxy.

16. A compound according to claim 15, namely 3-thiocarbamoyl-4,6-dimethoxyphenyl isothiocyanate.

17. A compound according to claim 15, namely 3-methylthiocarbamoyl-4,6-dimethoxyphenyl isothiocyanate.

18. A compound according to claim 15, namely 3-morpholinothiocarbonyl-4-methoxy-5-methylphenyl isothiocyanate.

* * * * *